US010821016B2

(12) United States Patent
Tsuchiya et al.

(10) Patent No.: US 10,821,016 B2
(45) Date of Patent: Nov. 3, 2020

(54) WRIST JOINT BANDAGE

(71) Applicant: KOWA COMPANY, LTD., Nagoya-shi (JP)

(72) Inventors: Akiharu Tsuchiya, Chuo-ku (JP); Hitoshi Ojima, Osaka (JP); Hidenori Kaseno, Kahoku (JP)

(73) Assignee: KOWA COMPANY, LTD., Nagoya-shi (JP)

( * ) Notice: Subject to any disclaimer, the term of this patent is extended or adjusted under 35 U.S.C. 154(b) by 950 days.

(21) Appl. No.: 15/123,605

(22) PCT Filed: Mar. 3, 2015

(86) PCT No.: PCT/JP2015/056223
§ 371 (c)(1),
(2) Date: Sep. 2, 2016

(87) PCT Pub. No.: WO2015/133480
PCT Pub. Date: Sep. 11, 2015

(65) Prior Publication Data
US 2017/0065449 A1    Mar. 9, 2017

(30) Foreign Application Priority Data

Mar. 3, 2014    (JP) .................................. 2014-040936

(51) Int. Cl.
*A61F 5/00*    (2006.01)
*A61F 13/00*    (2006.01)
(Continued)

(52) U.S. Cl.
CPC .......... *A61F 5/0118* (2013.01); *A61F 13/108* (2013.01)

(58) Field of Classification Search
CPC ........ A61F 13/108; A61F 5/0118; A61F 5/10; A61F 13/104; A61F 5/013; A61F 5/3715;
(Continued)

(56) References Cited

U.S. PATENT DOCUMENTS 3,238,939 A * 3/1966 Stubbs ................ A63B 71/146
128/DIG. 15
3,613,679 A * 10/1971 Bijou ................ A61F 13/00059
602/75
(Continued)

FOREIGN PATENT DOCUMENTS

JP        3122511 U    6/2006
JP    2009-167558 A    7/2009
(Continued)

OTHER PUBLICATIONS

Extended European Search Report dated Jul. 24, 2017 in Patent Application 15758134.9.
(Continued)

*Primary Examiner* — Kim M Lewis
(74) *Attorney, Agent, or Firm* — Oblon, McClelland, Maier & Neustadt, L.L.P.

(57) ABSTRACT

A wrist joint bandage includes a main body part including a woven fabric and having a band shape and a loop face, an anchor part joined to one end of the main body part, and an engaging part joined to the other end of the main body part and having a hook face such that the hook face detachably sticks to the loop face. The main body part has a winding part on one end side of the main body part and a supporting part on the other end side such that the winding part has a straight line shape and winds around a wrist of the wearer and that the supporting part has a straight line shape and extends from the back of the hand or the palm to the wrist. The supporting part and the winding part have the straight line shapes having the same width.

20 Claims, 9 Drawing Sheets

(51) Int. Cl.
*A61F 5/01* (2006.01)
*A61F 13/10* (2006.01)

(58) Field of Classification Search
CPC ......... A61F 5/3723; D01B 1/104; D01B 1/18; D01B 1/265; D01B 21/14
USPC .............................. 602/21, 64; D24/189, 190
See application file for complete search history.

(56) References Cited

U.S. PATENT DOCUMENTS

| | | | |
|---|---|---|---|
| 4,207,885 A * | 6/1980 | Hampton | A61F 13/00021 139/419 |
| 4,632,105 A * | 12/1986 | Barlow | A61F 13/108 602/64 |
| 4,991,234 A * | 2/1991 | Greenberg | A41D 20/00 2/16 |
| 5,188,356 A | 2/1993 | Furr et al. | |
| 5,685,787 A * | 11/1997 | Kogut | A63B 69/3608 473/205 |
| D403,425 S * | 12/1998 | Taylor | D24/192 |
| 5,916,187 A * | 6/1999 | Brill | A61F 5/0118 128/879 |
| 6,142,966 A * | 11/2000 | Hely | A61F 5/0118 128/879 |
| 6,783,507 B1 * | 8/2004 | Fisher | A61F 5/0118 602/21 |
| 7,037,286 B1 * | 5/2006 | Reinhardt | A61F 5/0118 128/878 |
| D620,058 S * | 7/2010 | Gaedke | D21/662 |
| 8,062,241 B2 * | 11/2011 | Bonutti | A61F 5/0104 602/4 |
| 8,480,502 B2 * | 7/2013 | Korte | A63B 69/0046 473/62 |
| 8,679,045 B2 * | 3/2014 | Dao | A61F 5/0118 602/20 |
| 8,702,634 B2 * | 4/2014 | Crompton | A61F 5/0118 128/879 |
| 2004/0054308 A1 * | 3/2004 | Herzberg | A61F 5/0109 602/21 |
| 2004/0210179 A1 | 10/2004 | Fisher | |
| 2013/0253400 A1 | 9/2013 | Massa | |
| 2014/0276322 A1 * | 9/2014 | Murphy | A61K 33/30 602/48 |

FOREIGN PATENT DOCUMENTS

| | | |
|---|---|---|
| JP | 2009-211268 A | 9/2009 |
| JP | 2010-29501 A | 2/2010 |
| JP | 2010-265556 A | 11/2010 |
| JP | 2011-45628 A | 3/2011 |
| JP | 3167617 U | 5/2011 |
| JP | 2014-152425 A | 8/2014 |
| WO | WO 01/34070 A1 | 5/2001 |

OTHER PUBLICATIONS

International Search Report dated Apr. 14, 2015 in PCT/JP15/056223 Filed Mar. 3, 2015.

* cited by examiner

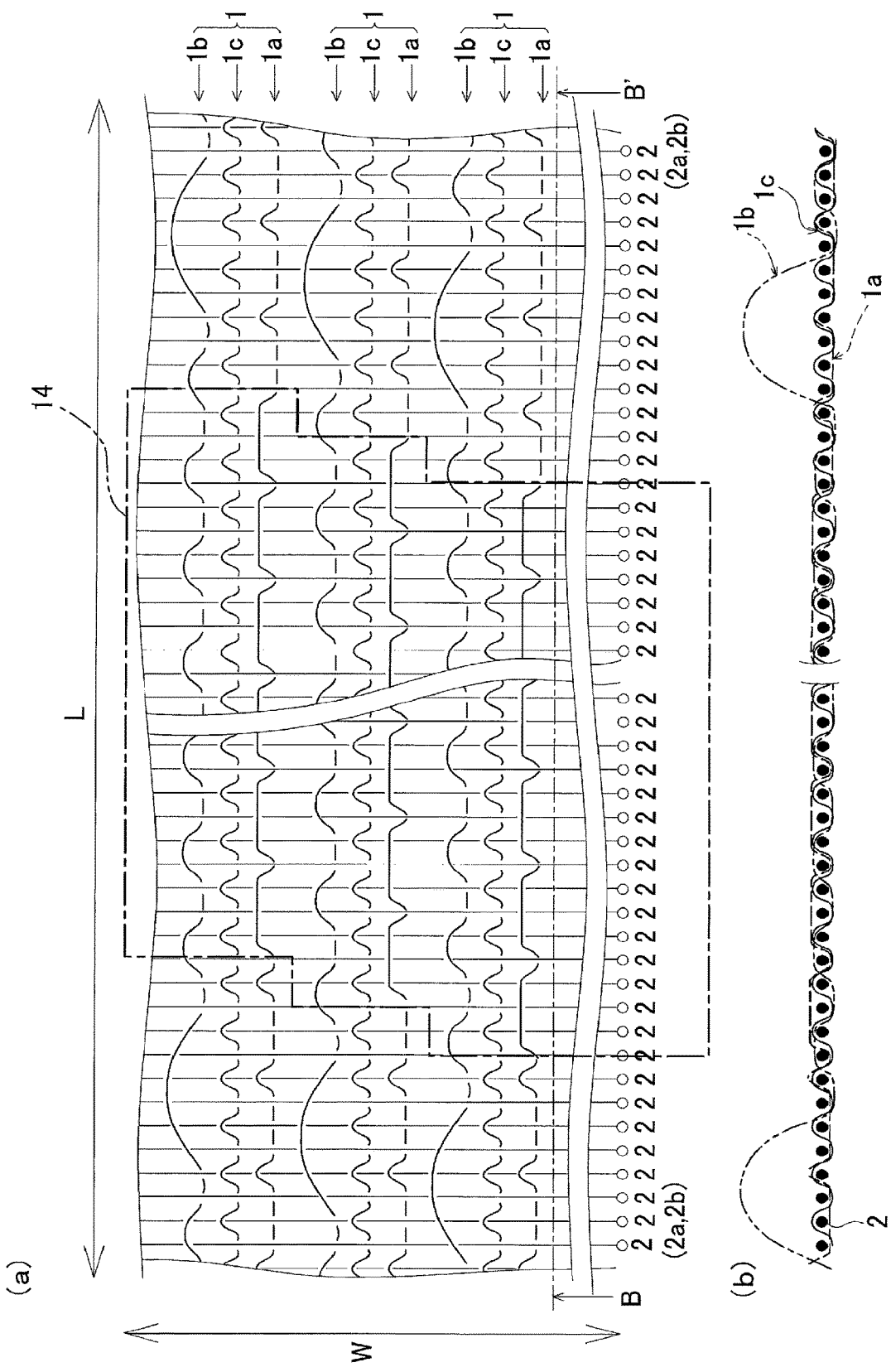

Fig. 7

| Evaluation items | Comparative Example 1 (35%) | Example 1 (45%) | Example 2 (60%) | Example 3 (75%) | Comparative Example 2 (90%) | Comparative Example 3 (130%) |
|---|---|---|---|---|---|---|
| ① Fixing force | Considerably strong (3.0 points) | Strong (2.4 points) | Strong (2.0 points) | Weak (1.2 points) | Weak (1.2 points) | Weak (1.4 points) |
| ② Pain | Painful (1.2 points) | Painful (1.2 points) | Almost painless (1.8 points) | Almost painless (1.8 points) | Painless (2.8 points) | Painless (2.6 points) |
| ③ Ease of peeling-off of touch fastener | Very good (3.0 points) | Very good (2.8 points) | Very good (2.8 points) | Good (2.2 points) | Poor (1.2 points) | Poor (1.0 point) |
| ④ Close contact property of fabric | With floating (1.0 points) | With floating (1.2 points) | Very good (2.8 points) | Very good (3.0 points) | Very good (3.0 points) | With floating (1.0 points) |
| ⑤ Ease of winding | Hard to wind (1.2 points) | Easy to wind (2.4 points) | Very easy to wind (2.6 points) | Easy to wind (2.4 points) | Hard to wind (1.2 points) | Hard to wind (1.0 points) |
| ⑥ Ease of adjustment of fixing force | Hard to adjust (1.0 points) | Easy to adjust (2.0 points) | Very easy to adjust (2.6 points) | Easy to adjust (2.0 points) | Hard to adjust (1.0 points) | Hard to adjust (1.0 points) |
| ⑦ Difficulty of fabric folding | Hard to be folded (3.0 points) | Hard to be folded (3.0 points) | Hard to be folded (2.8 points) | Slightly easy to be folded (2.2 points) | Easy to be folded (1.2 points) | Easy to be folded (1.2 points) |
| Total points | 13.4 points | 15.0 points | 17.4 points | 14.8 points | 11.6 points | 9.2 points |
| Average score | 1.91 points | 2.14 points | 2.49 points | 2.11 points | 1.66 points | 1.31 points |

WRIST JOINT BANDAGE

TECHNICAL FIELD

The present invention relates to a wrist joint bandage capable of supporting the daily motion of a wearer, and in particular, to a wrist joint bandage having a taping function of improving the stability of a wrist joint, thereby reducing a burden on the wrist joint, and preventing tenosynovitis of the hand.

BACKGROUND ART

In the past, a band-shaped taping tape (a stretchable or non-stretchable adhesive cloth tape which is used to be stuck to a part of the body), a bandage, a substantially tubular supporter knitted in circular knitting, or the like has been used in order to cope with a medical purpose such as for prevention of an external injury such as a sprain of a wrist joint, an ankle joint, or a knee joint, emergency treatment at the time of the external injury, assistance in rehabilitation after the injury and until complete recovery, or prevention of recurrence of the external injury or the like.

Of these, the taping tape is disposable, thereby is not economical, and has a problem in which depending on the constitution of a user, a rash occurs on the skin of the user due to an adhesive, and there is a concern that in a user having a sensitive skin, such as an aged person, skin peeling may occur when peeling off the taping tape.

Further, the circular knitting supporter has an approximately tubular shape, and therefore, there is a problem in which there is a concern that in a case where an injured site is inserted to be forcedly bent, it may be painful, and a fixing force is inferior, compared to the taping tape.

In contrast, the bandage is a band-shaped fabric having stretchability in a warp direction, and therefore, it easily follows an affected area, the wearer themselves can apply it while adjusting a fixing force, an excessive force is not applied against the movement of the wearer's body, a stable fixing force can be obtained, and it is economical because it can be used repeatedly.

For example, a wrist correction implement of the related art is provided with a locking part which is locked to the thumb or another finger of the hand, a band-shaped annular winding part which is fixed to be annularly wound around the wrist and has flexibility to expand and contract along a direction of the winding, and a band-shaped spiral winding part which connects the locking part and the annular winding part, is spirally wound over an area from the thumb or another finger of the hand to the wrist, and has flexibility to expand and contract along a direction of the winding (refer to PTL 1, for example).

CITATION LIST

Patent Literature

[Ptl 1] Jp-a-2011-45628

SUMMARY OF INVENTION

Technical Problem

In the wrist correction implement of the related art, the spiral winding part (the locking part) and the annular winding part are integrated to be continuous in a band shape, and therefore, the materials of the spiral winding part and the annular winding part are the same, and the spiral winding part and the annular winding part have the same maximum elongation (percentage of the difference between the longest length (an elongation dimension) when having been stretched with the highest load and the original length (a lay-flat size) with respect to the original length). In particular, in the wrist correction implement of the related art, in a case where an elongation rate of the spiral winding part is restrained in order to obtain a desired effect as a correction implement, the maximum elongation of a cloth (the spiral winding part) around the locking part into which a finger is inserted is also lowered, and the degree of freedom of deformation or the like of the locking part (a hole) associated with the extension of the cloth is lowered, and thus there is a problem in which floating or wrinkles of the cloth in the vicinity of the locking part occurs or a pain is caused in the finger inserted into the locking part.

Further, in PTL 1, there is a description to the effect that the spiral winding part and the annular winding part of the wrist correction implement are not limited to the same integrated structure and may have different structures, like a spiral winding part and an annular winding part of a knee correction implement or an elbow correction implement. However, there is no description regarding a difference in maximum elongation between the spiral winding part and the annular winding part. In particular, the locking part is fabricated by processing the spiral winding part, affects the maximum elongation of the spiral winding part regardless of whether the spiral winding part and the annular winding part are integrated or are separate bodies, and has the above-described problem.

The present invention has been made in order to solve the problem as described above and has an object to provide a wrist joint bandage in which it is possible to reduce a burden on the wrist joint by improving the stability of the wrist joint while providing a degree of freedom to a locking part (an anchor part) into which a finger is inserted.

Solution to Problem

According to the present invention, there is provided a wrist joint bandage including: a band-shaped main body part which is woven in a fabric having a loop face of a touch fastener and is composed of a winding part which is wound around the wrist of a wearer, and a supporting part which is disposed from the back of the hand or the palm to the wrist of the wearer; an anchor part which is joined to one end of the main body part and into which a finger of the wearer is inserted; and an engaging part which is joined to the other end of the main body part and has a hook face of a touch fastener, which is detachably stuck to the loop face of the main body part.

In addition, in the present invention, the expression "being disposed" means "being placed to be applied to a predetermined position of a person (a site of a wearer)", and the expression "being provided" means "being provided at a predetermined position of an object (a wrist joint bandage)".

Advantageous Effects of Invention

In the wrist joint bandage according to the present invention, it is possible to reduce a burden on the wrist joint by improving the stability of the wrist joint while providing a degree of freedom to the anchor part into which a finger is inserted.

BRIEF DESCRIPTION OF DRAWINGS

FIG. 6(a) is an explanatory diagram for describing an example of a fabric weave of a loop face and a pattern part of the main body part shown in FIG. 2, and FIG. 6(b) is a cross-sectional view taken along line B-B' and viewed in the direction of an arrow, of the fabric weave shown in FIG. 6(a).

FIG. 7 is a table showing the evaluation results of an effect feeling due to a difference in the maximum elongation of the main body part shown in FIG. 1.

DESCRIPTION OF EMBODIMENTS

First Embodiment of the Present Invention

Figure 1:
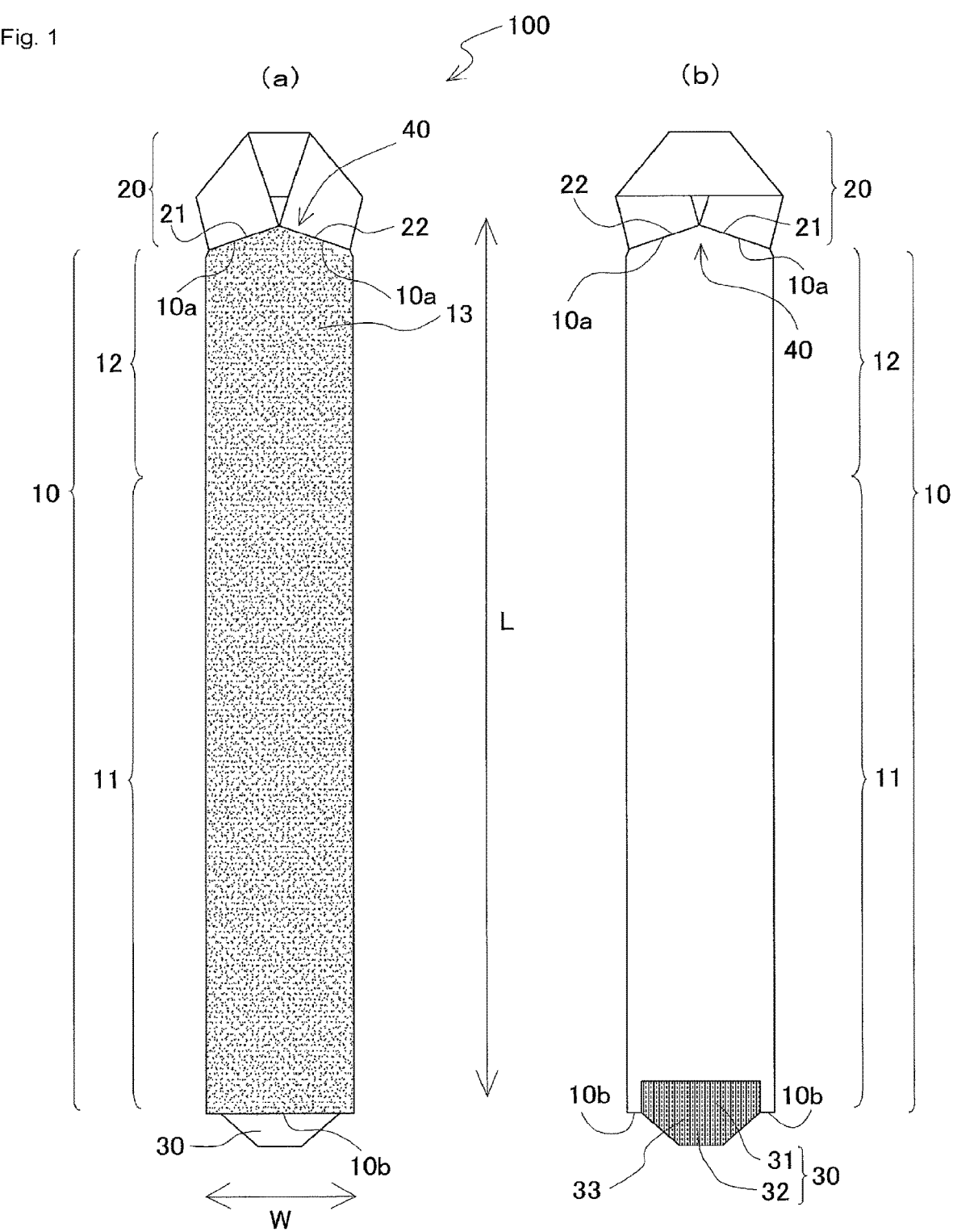
FIG. 1(a) is a front view showing a schematic configuration of a wrist joint bandage according to a first embodiment.
FIG. 1(b) is a back view of the wrist joint bandage shown in FIG. 1(a).

In the present invention, a bandage means a "thing which includes a band-shaped fabric having stretchability in a warp direction as a main material and in which the band-shaped fabric is wound around a part of the body, thereby being able to assist a function of the body", and as long as it has such an effect, even if it is not expressed as a bandage (for example, a taping supporter, a supporter band, or the like), it is within the scope of the bandage according to the present invention.

A wrist joint bandage 100 according to the present invention comprises: a band-shaped main body part 10 which is woven in a fabric having a loop face 13 of a touch fastener and is composed of a winding part 11 which is wound around the wrist of a wearer and a supporting part 12 which is disposed in a taut state from the back of the hand or the palm to the wrist of the wearer; an anchor part 20 which is joined to one end 10a of the main body part 10 and into which a finger of the wearer is inserted; and an engaging part 30 which is joined to the other end 10b of the main body part 10 and has a hook face 33 of a touch fastener, which is detachably stuck to the loop face 13 of the main body part 10, as shown in FIGS. 1 to 4. Further, the wrist joint bandage 100 is a bandage for both the right and left hands which can be worn on the wrist of either of the right hand or the left hand of the wearer.

The main body part 10 is made of a narrow stretchable fabric which is woven in combination of a warp 1 and a weft 2 by a power loom such as a needle loom or a jacquard needle loom, has stretchability in a warp direction (a longitudinal direction L), and is inhibited in stretchability in a weft direction (a width direction W).

Further, the main body part 10 is composed of the winding part 11 which is wound around the wrist of a wearer, and the supporting part 12 which is disposed in a taut state from the back of the hand or the palm to the wrist of the wearer, in which the supporting part 12 is provided on the one end 10a side of the main body part 10, the winding part 11 is provided on the other end 10b side of the main body part 10, and the supporting part 12 and the winding part 11 have straight line shapes having the same width.

Figure 5:
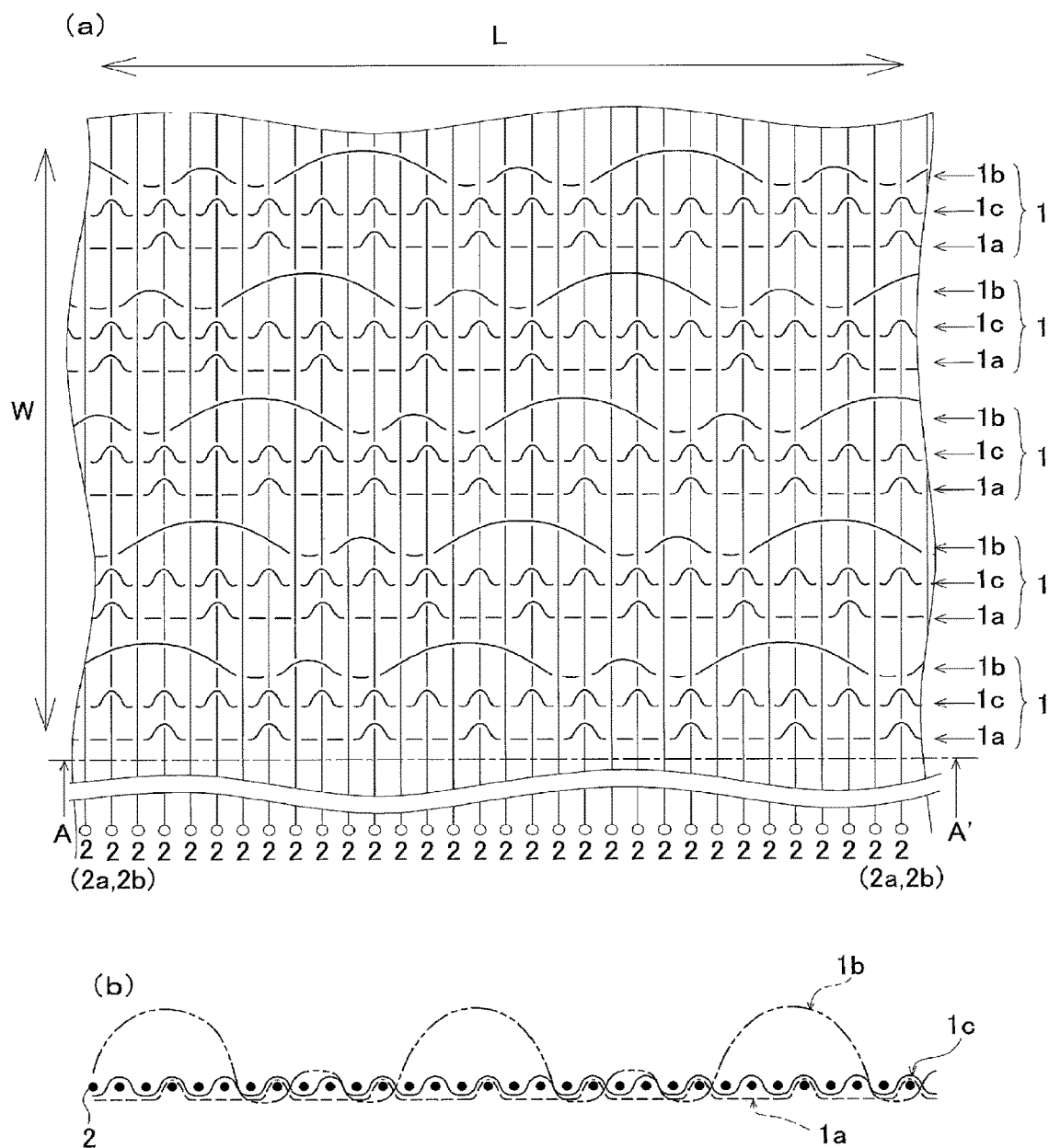
FIG. 5(a) is an explanatory diagram for describing an example of a fabric weave of a loop face of the main body part shown in FIG. 1.
FIG. 5(b) is a cross-sectional view taken along line A-A' and viewed in the direction of an arrow, of the fabric weave shown in FIG. 5(a).

Further, the warp 1 of the main body part 10 is provided with a warp ground yarn 1a which configures one face (for example, a back ground face) of a fabric along with the weft 2, a pile yarn 1b which forms loops on the other face (for example, a front ground face) of the fabric by floating on a plurality of wefts 2 adjacent to each other in the warp direction, and an elastic yarn 1c which provides stretchability in the warp direction, as shown in FIG. 5. Hereinafter, in this specification, a face having the loop face 13 is referred to as a "front ground face", and a back face thereof is referred to as a "back ground face".

The weft 2 is provided with a weft ground yarn 2a which configures the back ground face of the fabric along with the warp ground yarn 1a, and a fusion yarn 2b which is provided parallel to the weft ground yarn 2a and has thermal adhesiveness, and a single piece of weft ground yarn 2a and a single piece of fusion yarn 2b are provided in parallel, thereby configuring a single piece of weft 2. Further, in FIGS. 5 and 6, a single piece of weft ground yarn 2a and a single piece of fusion yarn 2b are shown as a single piece of weft 2. Further, in FIGS. 5(b) and 5(b), on the basis of the wefts 2 which are provided in parallel, the upper side is the front ground face and the lower side is the back ground face.

Figure 2:
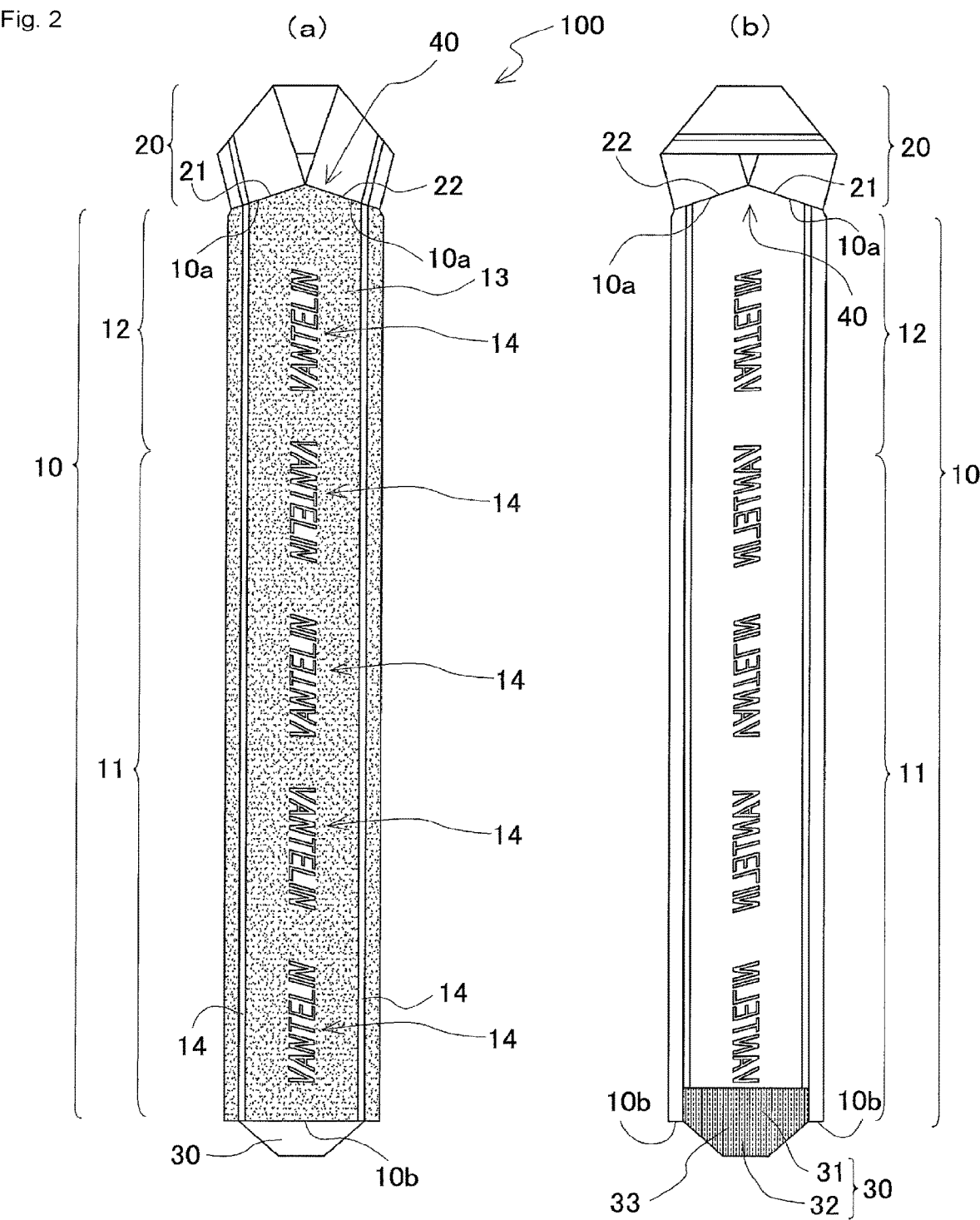
FIG. 2(a) is a front view showing a schematic configuration of a wrist joint bandage in which a pattern is formed in a main body part shown in FIG. 1.
FIG. 2(b) is a back view of the wrist joint bandage shown in FIG. 2(a).

Further, in the main body part 10, a pattern 14 composed of characters, figures, symbols, or a combination thereof can be partially formed in the front ground face in a jacquard weave which is freely opened, as shown in FIG. 2, by making the warp ground yarn 1a of the warp 1 float to the front ground face side and making the pile yarn 1b of the warp 1 sink to the back ground face, with respect to the plurality of wefts 2 adjacent to each other in the warp direction (the longitudinal direction L), by using a jacquard needle loom, and the main body part 10 has loops (the loop face 13) on substantially the entire surface of the front ground face with the exception of the regions of the patterns 14.

Next, an example of a fabric weave of the main body part 10 according to this embodiment will be described by using FIG. 5. That is, the warp ground yarn 1a forming the loop face 13 configures a fabric weave by repeating 1-3 float-sink with respect to the weft 2 (the weft ground yarn 2a and the fusion yarn 2b), in which the warp ground yarn 1a floats so as to pass on the upper side with respect to a single piece of weft 2 (weft ground yarn 2a and fusion yarn 2b) and sinks so as to pass on the lower side with respect to three pieces of wefts 2 (weft ground yarns 2a and fusion yarns 2b) adjacent to each other, as shown in FIG. 5(b).

Further, the pile yarn 1b forming the loop face 13 configures a fabric weave by repeating 6-2-2-2 float-sink with respect to the weft 2 (the weft ground yarn 2a and the fusion yarn 2b), in which the pile yarn 1b floats so as to pass on the upper side with respect to six pieces of wefts 2 (weft ground yarns 2a and fusion yarns 2b) adjacent to each other, sinks so as to pass on the lower side with respect to two pieces of wefts 2 (weft ground yarns 2a and fusion yarns 2b) adjacent to each other, floats so as to pass on the upper side with respect to two pieces of wefts 2 (weft ground yarns 2a and fusion yarns 2b) adjacent to each other, and sinks so as to pass on the lower side with respect to two pieces of wefts 2 (weft ground yarns 2a and fusion yarns 2b) adjacent to each other, as shown in FIG. 5(b).

Further, the elastic yarn 1c forming the loop face 13 configures a fabric weave by repeating 1-1 float-sink with respect to the weft 2 (the weft ground yarn 2a and the fusion yarn 2b), in which the elastic yarn 1c floats with respect to a single piece of weft 2 (weft ground yarn 2a and fusion yarn 2b) and sinks with respect to a single piece of weft 2 (weft ground yarn 2a and fusion yarn 2b), as shown in FIG. 5(b).

In addition, the fabric weave composed of the warp ground yarn 1a, the pile yarn 1b, and the elastic yarn 1c shown in FIG. 5 is an example, and as long as it is possible to have loops (the loop face 13) on the front ground face, there is no limitation to this fabric weave.

Subsequently, an example of a fabric weave of the pattern 14 which is formed in the main body part 10 according to this embodiment will be described by using FIG. 6. That is, the warp ground yarn 1a forming the pattern 14 configures a fabric weave by repeating 3-1 float-sink with respect to the weft 2 (the weft ground yarn 2a and the fusion yarn 2b), in which the warp ground yarn 1a floats so as to pass on the upper side with respect to three pieces of wefts 2 (weft ground yarns 2a and fusion yarns 2b) adjacent to each other and sinks so as to pass on the lower side with respect to a single piece of weft 2 (weft ground yarn 2a and fusion yarn 2b), as shown in FIG. 6(b).

Further, the pile yarn 1b forming the pattern 14 configures a fabric weave by repeating 2-2 float-sink with respect to the weft 2 (the weft ground yarn 2a and the fusion yarn 2b), in which the pile yarn 1b sinks so as to pass on the lower side with respect to two pieces of wefts 2 (weft ground yarns 2a and fusion yarns 2b) adjacent to each other and floats so as to pass on the upper side with respect to two pieces of wefts 2 (weft ground yarns 2a and fusion yarns 2b) adjacent to each other, as shown in FIG. 6(b).

Further, the elastic yarn 1c forming the pattern 14 configures a fabric weave by repeating 1-1 float-sink with respect to the weft 2 (the weft ground yarn 2a and the fusion yarn 2b), in which the elastic yarn 1c floats so as to pass on the upper side with respect to a single piece of weft 2 (weft ground yarn 2a and fusion yarn 2b) and sinks so as to pass on the lower side with respect to a single piece of weft 2 (weft ground yarn 2a and fusion yarn 2b), as shown in FIG. 6(b).

In addition, the fabric weave composed of the warp ground yarn 1a, the pile yarn 1b, and the elastic yarn 1c shown in FIG. 6 is an example, and as long as it is possible to form the pattern 14 in the loop face 13 of the front ground face, there is no limitation to this fabric weave.

Further, in the main body part 10, it is possible to freely adjust the maximum elongation in the warp direction (the longitudinal direction L) by the quality of the materials of the warp 1 and the weft 2 (in particular, the thicknesses of the elastic yarn 1c and the weft ground yarn 2a) and the number of times of picking (the number) of the weft 2. In the present invention, the maximum elongation refers to the "percentage of the difference between the longest length (an elongation dimension) when having been stretched with the highest load and the original length (a lay-flat size) with respect to the original length".

In particular, from the results of the overall determination of a sensory evaluation which will be described later, it is preferable that the maximum elongation in the warp direction (the longitudinal direction L) of the main body part 10 according to this embodiment is set to be in a range of 40% to 80%, and a range of 45% to 75% is more preferable, and the most preferred is 60%.

Here, an embodiment of the main body part 10 in which the maximum elongation is set to be 60% will be described. With respect to the warp ground yarn 1a of the main body part 10 according to this embodiment, a woolly nylon two-ply yarn having a thickness of 100 counts is preferable, and in the main body part 10 according to this embodiment, it is preferable to use 132 pieces of woolly nylon two-ply yarns.

Further, the pile yarn 1b of the main body part 10 according to this embodiment is a special textured yarn (210 D-10F) obtained by twisting 10 pieces of nylon filaments together, then applying heat thereto, and further performing twisting in a direction opposite to the twisting direction of the 10 pieces of nylon filaments, and having a thickness of 210 deniers, and in the main body part 10 according to this embodiment, it is preferable to use 132 pieces of special textured yarns (210 D-10F).

Further, with respect to the elastic yarn 1c of the main body part 10 according to this embodiment, a polyurethane yarn having a thickness of 560 deniers is preferable, and in the main body part 10 according to this embodiment, it is preferable to use 36 pieces of polyurethane yarns.

That is, in the main body part 10 in the quality of the material of the warp 1 described above, for example, if a width is 5 cm, warp density by the warps 1 (the warp ground yarns 1a, the pile yarns 1b, and the elastic yarns 1c) is 1485.6 D/mm(=((210 D×132 pieces)+(100 D×2 pieces×132 pieces)+(560 D×36 pieces))/50 mm).

Further, in the pile yarn 1b of the main body part 10 according to this embodiment, a filament count is 10 pieces, whereby there is an advantage that, compared to a case where a filament count is a low count (for example, 7 pieces), an adhesive force between dense filaments is high and a feel of the fabric (the main body part 10) is soft.

Further, the elastic yarn 1c of the main body part 10 according to this embodiment has a thickness of 560 deniers, thereby making the thickness of the fabric (the main body part 10) thin, compared to the case of a thick elastic yarn (for example, 1120 deniers), and thus it is possible to soften the fabric itself.

Further, with respect to the weft ground yarn 2a of the main body part 10 according to this embodiment, it is preferable to use a single piece of polyester woolly yarn (EW) having a thickness of 150 deniers.

Further, with respect to the fusion yarn 2b of the main body part 10 according to this embodiment, it is preferable to use a single piece of nylon thermal fusion yarn (for example, "Elder (registered trademark)" manufactured by Toray Industries, Inc.) having a thickness of 100 deniers.

Further, in the main body part 10 according to this embodiment, a single piece of weft ground yarn 2a and a single piece of fusion yarn 2b are simultaneously picked as the weft 2 by a power loom, and the number of times of picking (the number) of the weft 2 (the weft ground yarn 2a and the fusion yarn 2b) is 36.9 times (each 36.9 pieces) per 2.54 cm (1 inch).

That is, in the main body part 10 in the quality of material and the number of times of picking (the number) of the weft 2 described above, weft density by the wefts 2 (the polyester woolly yarns and the nylon thermal fusion yarns) is 9225 D/inch(=(150 D+100 D)×36.9 times/inch).

Further, the weft ground yarn 2a of the weft 2 of the main body part 10 according to this embodiment has a thickness of 150 deniers, whereby it is possible to make the thickness of the fabric (the main body part 10) thin, compared to the case of a weft ground yarn (for example, 300 deniers) which is a thick weft.

In this manner, in the main body part 10 according to this embodiment, due to the quality of the materials of the warp 1 and the weft 2 (in particular, the thicknesses of the elastic yarn 1c and the weft ground yarn 2a) described above and the number of times of picking (the number) of the weft 2 described above, it is possible to set the maximum elongation in the warp direction (the longitudinal direction L) to be 60%.

Further, with respect to the thickness of the elastic yarn 1c according to this embodiment, 560 deniers has been given as an example. However, in the present invention, available (mass-producible) 420 deniers which is a thickness lower by 1 rank, or 1120 deniers which is a thickness higher by 1 rank may be selected, and the thickness and the number of times of picking (the number) of the weft 2 described above may be changed. That is, if the thickness of the elastic yarn 1c according to this embodiment is in a range of 420 deniers to 1120 deniers, it is possible to set the maximum elongation in the warp direction of the main body part 10 to be the maximum elongation within the above-described range.

Further, with respect to the thickness of the weft ground yarn 2a of the weft 2 according to this embodiment, 150 deniers has been given as an example. However, in the present invention, available (mass-producible) 100 deniers which is a thickness lower by 1 rank, or 300 deniers which is a thickness higher by 1 rank may be selected, and the thickness of the elastic yarn 1c and the number of times of picking (the number) of the weft 2 described above may be changed. That is, if the thickness of the weft ground yarn 2a of the weft 2 according to this embodiment is in a range of 100 deniers to 300 deniers, it is possible to set the maximum elongation in the warp direction of the main body part 10 to be the maximum elongation within the above-described range.

Further, with respect to the number of times of picking (the number) of the weft 2 (the weft ground yarn 2a and the fusion yarn 2b) according to this embodiment, 36.9 times (each 36.9 pieces) per 2.54 cm (1 inch) has been given as an example. However, in the present invention, the number of times of picking (the number) of the weft 2 (the weft ground yarn 2a and the fusion yarn 2b) in a range of 32.8 times (each 32.8 pieces) per 2.54 cm to 41.0 times (each 41.0 pieces) per 2.54 cm may be selected, and the thicknesses of the elastic yarn 1c and the weft 2 described above may be changed. That is, if the number of times of picking (the number) of the weft 2 (the weft ground yarn 2a and the fusion yarn 2b) according to this embodiment is in a range of 32.8 times (each 32.8 pieces) per 2.54 cm to 41.0 times (each 41.0 pieces) per 2.54 cm, it is possible to set the maximum elongation in the warp direction of the main body part 10 to be the maximum elongation within the above-described range.

Further, in a case where the thickness of the main body part 10 is too thick, when winding the bandage around a part of the body of a wearer, it becomes bulky, and thus it becomes difficult to wind it, and in a case where the thickness of the main body part 10 is too thin, the fabric itself of the bandage is easily foldable, and thus a desired fixing force is not obtained. For this reason, it is preferable that the thickness of the main body part 10 is set to be a thickness in which it is easy to wind the bandage and a desired fixing force is obtained, and for example, if the maximum elongation in the warp direction (the longitudinal direction L) of the main body part 10 is 60%, it is preferable to set the thickness of the main body part 10 to be less than or equal to 3 mm.

Further, in the main body part 10 according to this embodiment, the loop face 13 is provided on a face (the front ground face) which becomes the outside in a case where the main body part 10 has been wound around the wrist of a wearer, and therefore, the engaging part 30 (the hook face 33) provided at the main body part 10 is provided on the back ground face side of the other end 10b of the main body part 10 in terms of the ease of attachment and detachment and the degree of freedom of an engaging position.

Further, in the main body part 10, the length of a portion (the supporting part 12) which supports the back of the hand or the palm of a wearer, and the length of a portion (the winding part 11) which circles around the wrist of the wearer at least once in order to protect the wrist of the wearer are required, and although there is an individual difference in the size of the hand according to gender, age, or the like, it is preferable to set the length of the main body part 10 to be in a range of 28 cm to 33 cm, for example. Further, in the main body part 10, a certain level of width is required in order to effectively perform the treatment of tenosynovitis (the fixing of the wrist joint) of the wearer, and it is preferable to set the width to be in a range of 3 cm to 7 cm, for example.

The anchor part 20 is for positioning the wrist joint bandage 100 with respect to the wrist joint of a wearer by inserting a finger of the wearer therein, and preventing position shift by suppressing the rotational movement in a winding direction of the main body part 10 with respect to the wrist of the wearer.

The anchor part 20 is made of a narrow stretchable fabric which is woven in combination of the warp 1 and the weft 2 by a power loom such as a needle loom or a jacquard needle loom, has stretchability in the warp direction (a circumferential direction or a longitudinal direction), and is inhibited in stretchability in the weft direction (a width direction). Further, the anchor part 20 according to this embodiment is woven by a needle loom, because the pattern 14 is not formed therein.

Further, the warp 1 of the anchor part 20 is provided with the warp ground yarn 1a which configures one face (for example, the back ground face) of the fabric along with the weft 2, and the elastic yarn 1c which provides stretchability in the warp direction.

Further, with respect to the warp ground yarn 1a of the anchor part 20 according to this embodiment, a woolly nylon two-ply yarn having a thickness of 70 counts is preferable, and in the anchor part 20 according to this embodiment, it is preferable to use 184 pieces of woolly nylon two-ply yarns.

Further, with respect to the elastic yarn 1c of the anchor part 20 according to this embodiment, a polyurethane yarn having a thickness of 840 deniers is preferable, and in the anchor part 20 according to this embodiment, it is preferable to use 27 pieces of polyurethane yarns.

That is, in the anchor part 20 in the quality of the material of the warp 1 described above, for example, if a width is 3 cm, warp density by the warps 1 (the warp ground yarns 1a and the elastic yarns 1c) is 1614.66 D/mm(=((70 D×2 pieces×184 pieces)+(840 D×27 pieces))/30 mm).

Further, with respect to the weft ground yarn 2a of the anchor part 20 according to this embodiment, it is preferable to use a single piece of polyester woolly yarn having a thickness of 150 deniers, and in the anchor part 20 according to this embodiment, the number of times of picking (the number) of the weft 2 (the weft ground yarn 2a) is 33.9 times (33.9 pieces) per 2.54 cm (1 inch).

That is, in the anchor part 20 in the quality of material and the number of times of picking (the number) of the weft 2 described above, weft density by the wefts 2 (the polyester woolly yarns) is 5085 D/inch(=150 D×33.9 times/inch).

In this manner, in the anchor part 20 according to this embodiment, due to the quality of the materials of the warp 1 and the weft 2 (in particular, the thicknesses of the elastic yarn 1c and the weft ground yarn 2a) described above and the number of times of picking (the number) of the weft 2 described above, the maximum elongation in the circumferential direction (the longitudinal direction or the warp direction) is set to be 240%. However, in general, it is preferable that the maximum elongation of the anchor part 20 is set to be in a range of 200% to 280%.

Further, in the wrist joint bandage 100, due to the maximum elongation in the circumferential direction (the longitudinal direction or the warp direction) of the anchor part 20 being greater than the maximum elongation in the longitudinal direction L (the warp direction) of the main body part 10, the stability of the wrist joint is improved by fixing the wrist joint by a tightening force of the main body part 10 while providing the flexibility of the anchor part 20, and thus it is possible to reduce a burden on the wrist joint.

Further, the anchor part 20 according to this embodiment is formed in a ring shape by joining (for example, sewing) both ends of a band-shaped body which is a stretchable fabric to one end 10a of the main body part 10, and therefore, the anchor part 20 is made as a separate member from the main body part 10, whereby it is possible to make the maximum elongation in the circumferential direction (the longitudinal direction or the warp direction) different from the maximum elongation in the longitudinal directionL (the warp direction) of the main body part 10 and it is possible to easily manufacture the wrist joint bandage 100.

In particular, the anchor part 20 according to this embodiment is joined to the main body part 10, thereby becoming a substantially conical tube having a tapered shape, in which a small-diameter portion is formed on the front ground face side of the main body part 10 and a large-diameter portion is formed on the back ground face side of the main body part 10, as shown in FIG. 3(e). In this way, in the wrist joint bandage 100, in a case where a finger of a wearer has been inserted into the anchor part 20, the inner surface of the anchor part 20 is fitted to the shape of the base of the finger, and thus it is possible to suppress the occurrence of floating or wrinkles in the anchor part 20.

Further, a joining portion 40 between the anchor part 20 and one end 10a of the main body part 10 is sewn convexly to the anchor part 20 side so as to become longer than the length in the width direction W of the main body part 10. In particular, one end 10a of the main body part 10 according to this embodiment protrudes in, for example, a mountain shape (an approximately dogleg shape) in which the lengths of two oblique sides with an apex angle of about 135 degrees therebetween are equal, as shown in FIG. 1, and one end 21 of the anchor part 20 is sewn to one oblique side, and the other end 22 of the anchor part 20 is sewn to the other oblique side. However, it is preferable that the apex angle is set to be in a range of 120 degrees to 150 degrees.

In this manner, in the wrist joint bandage 100, the joining portion 40 is sewn in a shape convex toward the anchor part 20, whereby in a case of winding the wrist joint bandage 100 around the wrist of a wearer, a twist at the joining portion 40 can be absorbed in response to the winding (pulling) direction of the main body part 10 and thus it is possible to suppress the occurrence of floating or wrinkles in the vicinity of the joining portion 40.

Further, with respect to the types of sewing, there are flat seamer sewing (four-needle sewing), overlock sewing, three-point zigzag sewing, and the like. However, the joining portion 40 according to this embodiment is sewn with the flat seamer sewing which has the advantage that a combined portion becomes thinner, a seam is finished to be flat and strong with a force pressing the seam, and it is easy to conform to a three-dimensional shape by cutting in a mountain shape, and because there is no seam allowance on the back face of a cloth, a sewing point does not touch the skin, and thus a feeling of wearing is good.

Further, in the anchor part 20, a certain level of length is required in order to insert one finger or a plurality of fingers of a wearer, and it is preferable to set the length to a length in a range of 7 cm to 11 cm, for example. Further, in a case where the width of the anchor part 20 is narrow, when a wearer wears the wrist joint bandage 100, pressure which is applied from the anchor part 20 to a locking portion of the fingers is increased due to the tensile stress from the main body part 10, and thus there is a case where a pain is caused in the finger. For this reason, with respect to the width of the anchor part 20, a certain level of width is required, and it is preferable to set the width to be in a range of 2 cm to 4 cm, for example.

The engaging part 30 according to this embodiment has a planar shape of a combination of, for example, a rectangle and an isosceles trapezoid, as shown in FIG. 1(b), in which a rectangular portion 31 is sewn to the back ground face of the main body part 10 and an isosceles trapezoid portion 32 protrudes from the other end 10b of the main body part 10. In this manner, in the engaging part 30, the isosceles trapezoid portion 32 protrudes from the other end 10b of the main body part 10, thereby becoming thinner by an amount that does not overlap the main body part 10, whereby it is easy to grip the isosceles trapezoid portion 32 with the fingers of a wearer, and thus it is possible to easily attach and detach the hook face 33 with respect to the loop face 13 of the main body part 10.

Figure 3:
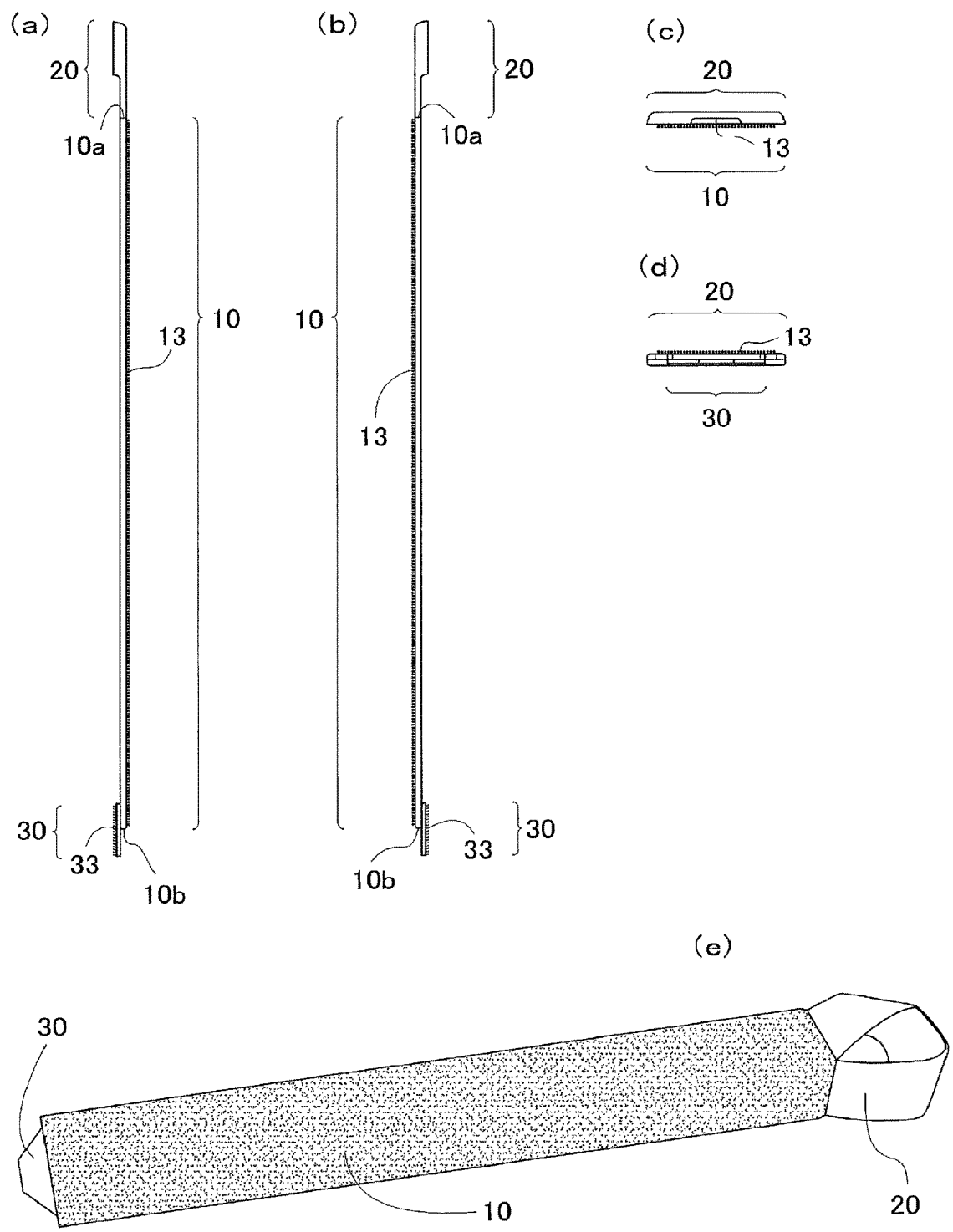
FIG. 3(a) is a left side view of the wrist joint bandage shown in FIG. 1(a)
FIG. 3(b) is a right side view of the wrist joint bandage shown in FIG. 1(a)
FIG. 3(c) is a plan view of the wrist joint bandage shown in FIG. 1(a)
FIG. 3(d) is a bottom view of the wrist joint bandage shown in FIG. 1(a)
FIG. 3(e) is a perspective view of the wrist joint bandage shown in FIG. 1.

Next, a method of wearing the wrist joint bandage 100 shown in FIGS. 1 and 3 will be described by using FIG. 4.

In addition, in the following description, a case of wearing the wrist joint bandage 100 on the left hand of a wearer will be described. However, in a case of wearing the wrist joint bandage 100 on the right hand of the wearer, the wearing method is the same as the wearing method on the left hand except that the winding direction of the main body part 10 on the wrist is the opposite direction.

A wearer hangs the anchor part 20 of the wrist joint bandage 100 on the first finger (the thumb) of the hand (inserts the first finger of the hand into the anchor part 20) in a state where the palm of the left hand is visible, as shown in FIG. 4(a).

Then, the wearer pulls the main body part 10 while gripping the other end 10b of the main body part 10 with the right hand and disposes the main body part 10 (the supporting part 12) in an extended state on the back side of the hand from the base of the first finger of the left hand to the part corresponding to the ulnar head. In addition, the extended state refers to a state of having an elongation margin allowing the wearer to finely adjust a winding position after the wearing of the wrist joint bandage 100.

Then, the wearer makes the main body part 10 (the winding part 11) in the extended state circle around the wrist from the part corresponding to the ulnar head of the left hand, as shown in FIGS. 4(b) and 4(c), and thereafter, makes the hook face 33 of the engaging part 30 which is located at the other end 10b of the main body part 10 be engaged with the loop face 13 of the main body part 10 (the winding part 11), as shown in FIGS. 4(d) and 4(e), whereby the wearing is completed.

Further, in the wearing method of the wrist joint bandage 100 described above, the finger of the wearer which is inserted into the anchor part 20 has been described as being the first finger. However, it is also possible to wear the wrist joint bandage 100 by inserting one finger or a plurality of fingers among other fingers (the second finger (the index finger or the forefinger), the third finger (the middle finger), the fourth finger (the ring finger), and the fifth finger (the little finger)) into the anchor parts 20.

Further, in the wearing method of the wrist joint bandage 100 described above, a case of winding the main body part 10 from the back side of the hand has been described. However, in a case where it is not possible to bend the first finger back to the back side of the hand, it is also possible to wear the wrist joint bandage 100 by winding the main body part 10 in the opposite direction from the palm side.

Next, the optimal range of the maximum elongation in the warp direction in the main body part 10 of the wrist joint bandage 100 according to this embodiment will be described based on the test results of a trial use test.

In addition, in the trial use test, as shown in FIG. 1, the wrist joint bandages 100 (hereinafter, respectively referred to as Example 1, Example 2, and Example 3) each provided with the main body part 10 (length: 33 cm, width: 5 cm) woven with the quality of the materials of the warp 1 and the weft 2 and the number of times of picking (the number) of the weft 2 shown in Table 1 below and having the maximum elongation of 45%, 60%, or 75%, the anchor part 20, and the engaging part 30 were fabricated and used.

Further, wrist joint bandages (hereinafter, respectively referred to as Comparative Example 1 and Comparative Example 2) were fabricated in the same manner as in the above examples by using the main body part 10 (length: 33 cm, width: 5 cm) having the maximum elongation of 35% or 90% and used in the trial use test.

Further, a commercially available wrist joint bandage (hereinafter referred to as Comparative Example 3) made with the quality of the materials of the warp 1 and the weft 2 and the number of times of picking (the number) of the weft 2 shown in Table 1 below was used in the trial use test.

In addition, Comparative Example 3 does not have a loop face as a touch fastener, and therefore, Comparative Example 3 is not provided with a pile yarn in a warp and a fusion yarn in a weft.

TABLE 1

|  | Quality of material | | | | | Number of times | |
|  | Warp | | | Weft | | of picking | Maximum |
|  | Warp ground yarn | Pile yarn | Elastic yarn | Weft ground yarn | Fusion yarn | (Number) of weft [times/inch] | elongation [%] |
| Example 1 | WN100/2 | 210D-10F | 560D | EW150D | Elder 100D | 39.8 | 45 |
| Example 2 | WN100/2 | 210D-10F | 560D | EW150D | Elder 100D | 36.9 | 60 |
| Example 3 | WN100/2 | 210D-10F | 560D | EW150D | Elder 100D | 33.8 | 75 |
| Comparative Example 1 | WN100/2 | 210D-10F | 560D | EW150D | Elder 100D | 42.3 | 35 |
| Comparative Example 2 | WN100/2 | 210D-10F | 560D | EW150D | Elder 100D | 30.8 | 90 |
| Comparative Example 3 | WN100/2 | — | 1120D | Nylon monofilament No. 1 | — | 37.0 | 130 |

Figure 4:
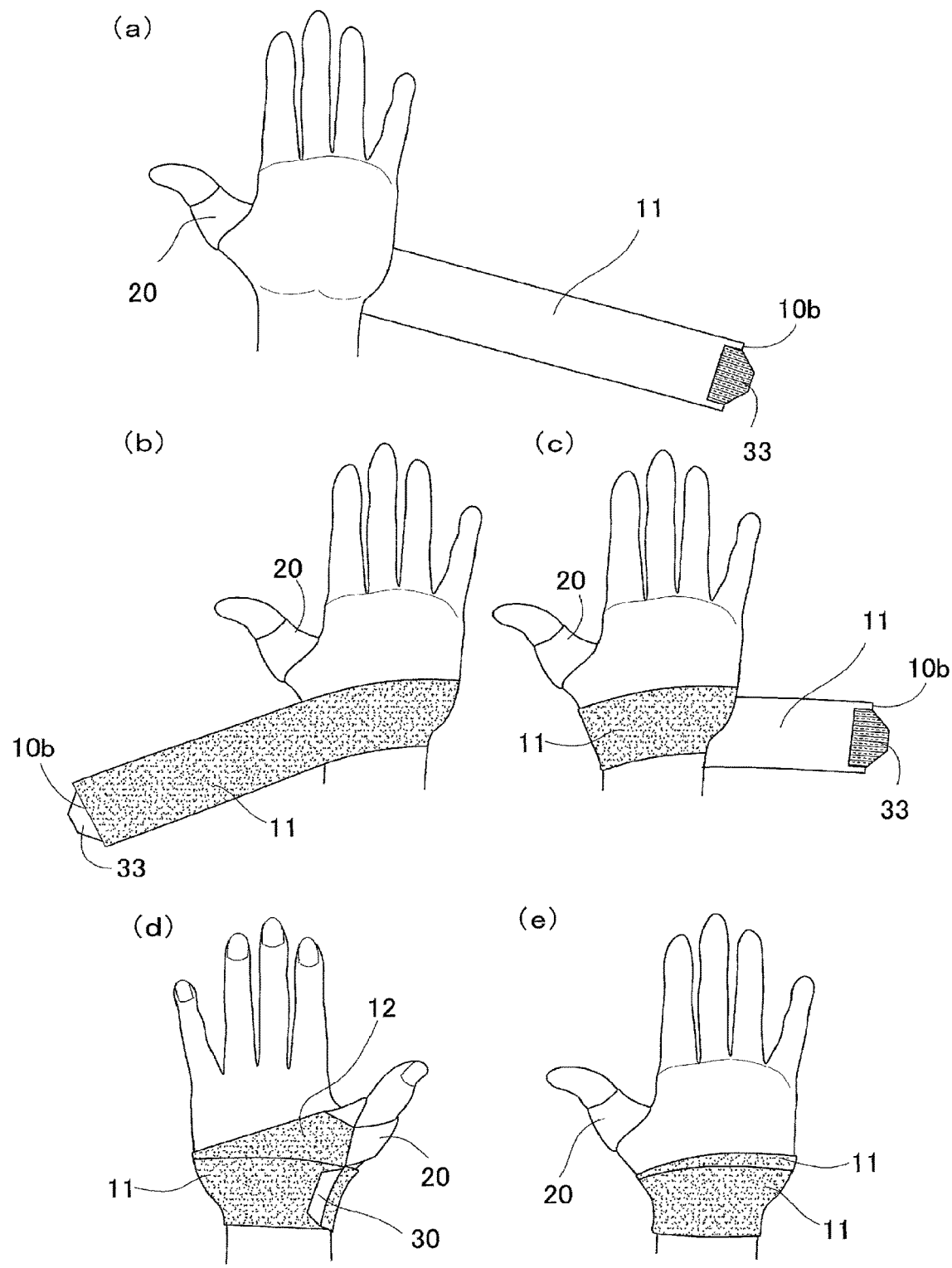
FIG. 4(a) is an explanatory diagram showing a state where a finger has been inserted into an anchor part of the wrist joint bandage shown in FIGS. 1 and 3.
FIG. 4(b) is an explanatory diagram showing a state where the main body part is half-turned from the part corresponding to the ulnar head of the left hand to the wrist.
FIG. 4(c) is an explanatory diagram showing a state where the main body part is further half-turned from the state shown in FIG. 4(b) to the wrist.
FIG. 4(d) is an explanatory diagram when the wearing state of the wrist joint bandage shown in FIGS. 1 and 3 is viewed from the back side of the hand.
FIG. 4(e) is an explanatory diagram when the wearing state of the wrist joint bandage shown in FIGS. 1 and 3 is viewed from the palm side.

In the trial use test, the wrist joint bandage was worn on the left hand of the wearer, as shown in FIG. 4, and the sensory evaluation (a total of five persons) of an effect feeling of the wearer in the evaluation items of FIG. 7 was carried out. In an evaluation method, first, the sensory evaluation for each evaluation item in each wearer was scored in three stages (3: very good, 2: good, and 1: poor), and the average score of all the wearers (5 persons) in each evaluation item was calculated. Thereafter, with respect to Examples 1 to 3 and Comparative Examples 1 to 3, the total points and the average score of each evaluation item were calculated, and comprehensively, the average score of two or more points was determined to be a passing mark.

Further, with respect to the evaluation item "fixing force" of FIG. 7, if it is a force restraining a range of motion of palmar flexion or dorsal flexion of the wrist joint, restraint of the range of motion of the palmar flexion or the dorsal flexion using a force more than necessary in a carry of luggage, in a case of using a strap of a train or a bus, during sports, in bedding drying, or in an operation of a clutch or the like of a motorcycle is supposed.

Further, if it is a force restraining a range of motion of radial flexion or ulnar flexion, restraint of the range of motion of the radial flexion or the ulnar flexion using a force more than necessary in motion of shaking a frying pan to the left and right, holding a cup, or shaking a fishing rod, during sports, or the like is supposed.

Further, with respect to the evaluation item "pain" of FIG. 7, if it is a pain due to a compression force of the fabric, in a case where the maximum elongation of the fabric is small, the fabric cannot follow the movement of a muscle or a joint or the expansion and contraction of the skin, and the compression force is more strongly felt, and thus it is considered that a pain is easily felt, and in a case where the maximum elongation of the fabric is large, it is considered that the fixing force to restrain the range of motion becomes weaker.

Further, if it is a rubbing pain due to the hardness of the fabric, in a case where the maximum elongation of the fabric is small, the fabric cannot follow the movement of a muscle or the skin, and therefore, rubbing occurs between the fabric and the skin, and thus it is considered that a pain is easily felt, and in a case where the maximum elongation of the fabric is large, the fabric extends so as to follow a muscle or the skin, and therefore, it is considered that trouble to the skin is less.

Further, with respect to the evaluation item "ease of peeling-off of touch fastener" of FIG. 7, a touch fastener being easily peeled off means that even a powerless wearer does not have difficulty in using a touch fastener and the fabric itself having the loop face of a touch fastener is hard, whereby it is difficult to lose a shape.

Further, a touch fastener being not easily peeled off means that at the time of the wearer's movement, there is no case where the hook face of a touch fastener is separated from the loop face due to the movement of a joint or the expansion of a muscle in a site on which the bandage is worn, whereas the pile yarns are pulled out from the fabric having the loop face of a touch fastener due to a strong engaging force between the hook face and the loop face of a touch fastener, and thus, in a case where a touch fastener is peeled off, the pile yarns project from the fabric, thereby causing fluffing of the fabric.

Further, with respect to the evaluation item "close contact property of fabric" of FIG. 7, in a case where the maximum elongation of the fabric is small, the fabric cannot follow the movement of a muscle or the skin, and therefore, a cloth does not come into close contact with the skin and skin resistance is reduced, and thus it is considered that the effect of the bandage is weakened, and in a case where the maximum elongation of the fabric is large, a cloth is easily fixed in close contact with the skin and fits to the movement of the skin or a muscle, and thus it is considered that the effect of the bandage is easily obtained.

Further, with respect to the evaluation item "ease of winding" of FIG. 7, in a case where the maximum elongation of the fabric is small, it is difficult for the fabric to conform to the curved surface of the skin, and thus it is difficult to wind the main body part 10. Further, in a case where the maximum elongation of the fabric is large, the fabric is easily fixed in close contact with the skin and easily fits to the movement of the skin or a muscle. However, it is difficult to feel the limit point of the elongation of the main body part 10, and therefore, the number of turns of the main body part 10 is increased and winding of the main body part 10 becomes difficult.

Further, with respect to the evaluation item "ease of adjustment of fixing force" of FIG. 7, in a case where the maximum elongation of the fabric is small, it is suitable for strong fixing. However, an adjustable range of the fixing force is narrow, and therefore, adjustment of the fixing force becomes difficult for a powerless wearer.

Further, with respect to the evaluation item "difficulty of fabric folding" of FIG. 7, in a case where the maximum elongation of the fabric is small, a texture is close, and therefore, there is also stiffness of the fabric, and thus it is difficult for the fabric to be folded. Further, in a case where the maximum elongation of the fabric is large, a texture is rough, and therefore, the fabric has an easily foldable weave, and thus it is considered that due to the fabric being folded, the structure of the main body part 10 is weakened.

In the evaluation items as described above, in Example 2, good evaluation results were obtained in almost all the evaluation items, as shown in FIG. 7.

Further, in Example 3, although the fixing force was weak, good evaluation results were obtained in other evaluation items.

Further, in Example 1, although there was a pain and the close contact property of the fabric was poor, good evaluation results were obtained in other evaluation items. In contrast, in Comparative Example 1, Comparative Example 2, and Comparative Example 3, poor evaluation results were obtained in most of the evaluation items.

From the above, as the overall evaluation results, it is found that Example 1 (maximum elongation: 45%), Example 2 (maximum elongation: 60%), and Example 3 (maximum elongation: 75%), in which the average score is two or more points, are optimal as the main body part 10.

That is, with respect to the maximum elongation in the warp direction in the main body part 10 of the wrist joint bandage 100 according to this embodiment, a range of 40% to 80% is preferable, a range of 45% to 75% is more preferable, and the most preferred is 60%.

Next, the main body part 10 of the wrist joint bandage 100 according to this embodiment will be described based on the test results of a durability test (peeling strength) of a touch fastener.

In addition, in the durability test (peeling strength) of a touch fastener, on the basis of Example 2 (the main body part 10 in which the maximum elongation in the warp direction is 60%) in which the most favorable results were obtained from the evaluation results of the above-described sensory evaluation, comparison with other stretchable fabrics was performed. Further, as comparative examples, in addition to Comparative Example 3 used in the above-described sensory evaluation, commercially available stretchable fabrics (hereinafter, respectively referred to as Comparative Example 4 and Comparative Example 5) made with the quality of the materials of the warp 1 and the weft 2 and the number of times of picking (the number) of the weft 2 shown in Table 2 below were used.

TABLE 2

| | Quality of material | | | | | Number of times of picking | | | |
|---|---|---|---|---|---|---|---|---|---|
| | Warp | | | Weft | | (Number) of | | | Maximum |
| | Warp ground yarn | Pile yarn | Elastic yarn | Weft ground yarn | Fusion yarn | weft [times/inch] | Thickness [mm] | Hardness | elongation [%] |
| Example 2 | WN100/2 | 210D-10F | 560D | EW150D | Elder 100D | 36.9 | 2.1 | Slightly soft | 60 |
| Comparative Example 3 | WN100/2 | — | 1120D | Nylon monofilament No. 1 | — | 37.0 | 1.7 | Soft | 130 |
| Comparative Example 4 | WN100/2 | 210D-7F | 1120D | EW300D | Elder 100D | 43.6 | 2.2 | Normal | 90 |
| Comparative Example 5 | WN100/2 | 210D-15F | 1120D | EW300D | Elder 100D | 25.8 | 3.3 | Hard | 100 |

Further, the major difference between Example 2 and Comparative Examples 3 to 5 is a difference in the filament count of the pile yarn, in which Example 2 has 10 pieces of filaments, whereas Comparative Example 4 has 7 pieces of filaments, Comparative Example 5 has 15 pieces of filaments, and Comparative Example 3 does not use a pile yarn (does not have a loop face of a touch fastener).

The durability test (peeling strength) of a touch fastener is based on Japanese Industrial Standards JIS L3416, "touch fastener", 7.4.2 "peeling strength", and the experimental results obtained by carrying out a repeat of adhesion and peeling 1000 times are shown in Table 3 below.

Further, the filament count of the pile yarn being high means that the hooks of a touch fastener are easily engaged with the loops and the retention rate is increased, while the maximum elongation is lowered.

In Comparative Example 5, the filament count of the pile yarn is higher than the filament count of the pile yarn of Example 2. However, resin processing is applied in order to prevent fluffing of external appearance, and therefore, it becomes difficult for the hooks of a touch fastener to be engaged with the loops, and the initial peeling strength and the retention rate become lower than the initial peeling strength and the retention rate of Example 2.

TABLE 3

| | Effective width of fastener [cm] | Peeling strength [N/cm] | | Retention rate [%] (peeling strength after durability test/initial peeling strength × 100) | Change in appearance after durability test |
|---|---|---|---|---|---|
| Example 2 | 4.7 | Initial After durability test | 0.358 0.649 | 181 | Loop elongation which is less (than in Comparative Example 5) is recognized. |
| Comparative Example 3 | 4.8 | Initial After durability test | 0.996 0.825 | 83 | Violent fluffing is recognized. |
| Comparative Example 4 | 4.7 | Initial After durability test | 0.281 0.254 | 90 | Noticeable change is not recognized. |
| Comparative Example 5 | 2.8 | Initial After durability test | 0.326 0.537 | 165 | Slight loop elongation is recognized. |

In Example 2, as shown in Table 3, the retention rate (the percentage of peeling strength after durability test with respect to initial peeling strength) is the highest, compared to Comparative Examples 3 to 5, and thus it is found that Example 2 is optimal as the main body part 10 which is used in the wrist joint bandage 100 which is wound around the wrist and then engaged by the hooks of a touch fastener.

In particular, in Example 2, the peeling strength after durability test becomes larger with respect to the initial peeling strength (the retention rate exceeds 100%), and therefore, Example 2 is advantageous in terms of a long-term continuing use as the wrist joint bandage 100.

As described above, the wrist joint bandage 100 fixes the wrist joint of a wearer with the main body part 10, and limits the palmar flexion of the wrist joint of the wearer in a case of being wound from the back side of the hand, and limits the dorsal flexion of the wrist joint of the wearer in a case of being wound from the palm side, whereby it is possible to secure the stability of the wrist joint and it is possible to reduce a load which is applied to a tendon which is located at the wrist joint.

In particular, in a case where the wrist joint bandage 100 is not worn, if there is a pain in the wrist joint, a burden is also applied to an elbow joint or the like which compensates for the overload on the wrist joint, and thus there is a concern that a secondary pain may be induced. For this reason, in a person who frequently uses the finger or the wrist joint and has a pain in the elbow or the front of the shoulder joint, the pain in the elbow or the shoulder joint, which results from the pain in the wrist joint in a chain reaction, can be reduced by the wearing of the wrist joint bandage 100.

Further, as the movement of the wrist joint, in addition to the palmar flexion or the dorsal flexion, there are radial flexion and ulnar flexion, and the radial flexion and the ulnar flexion are motions which are frequently used in everyday life, and as a result of these motions, a De Quervain syndrome which is an inflammation of the tendon extending toward the thumb from the hand occurs with increased frequency. In contrast, the wrist joint bandage 100 limits the radial flexion and the ulnar flexion of the wrist joint of a wearer, whereby prevention or improvement of the De Quervain syndrome can be expected.

Further, in the wrist joint bandage 100 shown in FIG. 2, for example, green yarns are used for the warp ground yarns 1*a* of the warps 1 of the main body part 10 and the anchor part 20, a black yarn is used for the pile yarn 1*b* of the warp 1 of the main body part 10, black yarns are used for the elastic yarns 1*c* of the warps 1 of the main body part 10 and the anchor part 20, black yarns are used for the wefts 2 of the main body part 10 and the anchor part 20, and as shown in FIG. 6, with respect to the shared weft 2, the warp ground yarn 1*a* is made to float and the pile yarn 1*b* is made to sink, whereby a green pattern 14 is formed on a black front ground face and the portion of the back ground face of the main body part 10, which corresponds to the pattern 14 of the front ground face of the main body part 10, appears as black on a green back ground face of the main body part 10.

Further, in the wrist joint bandage 100, there is no limitation to these colors, and for example, it is conceivable that a yarn having any one color of seven colors (red, orange, yellow, green, blue, indigo, and violet) which are the rainbow colors is used for the pile yarn 1*b* of the warp 1 of the main body part 10 and the front ground face except for the pattern 14 of the main body part 10 is made to have any one color of the rainbow colors. In this way, the wrist joint bandages 100 can encourage a consumer's willingness to buy with product groups with color variation of seven colors.

Further, in the wrist joint bandage 100, for example, the front ground face except for the pattern 14 of the main body part 10 is made to have a fluorescent color by using a fluorescent colored yarn for the pile yarn 1*b* of the warp 1 of the main body part 10, whereby a consumer's willingness to buy is encouraged, and the wrist joint bandage 100 is worn during going out at night, whereby it is visible by being illuminated by the headlights of an automobile or the like, and thus it can be expected to contribute to the safety and disaster prevention as well.

Further, a case where the main body part 10 according to this embodiment has the loop face 13 of a touch fastener has been described. However, a stretchable fabric which does not have the loop face 13 of a touch fastener is also acceptable.

In this case, the main body part 10 does not need the pile yarn 1*b* forming the loop face 13 and does not need the fusion yarn 2*b* holding the loops by the pile yarn 1*b*.

In particular, the main body part 10 according to this embodiment uses, instead of the pile yarn 1*b* configuring the warp 1, a warp ground yarn 1*a* (hereinafter referred to as a second warp ground yarn 1*d*) in which float-sink with respect to the weft 2 is reversed with respect to that in the above-described warp ground yarn 1*a* (hereinafter referred to as a first warp ground yarn 1*a*).

Figure 8:
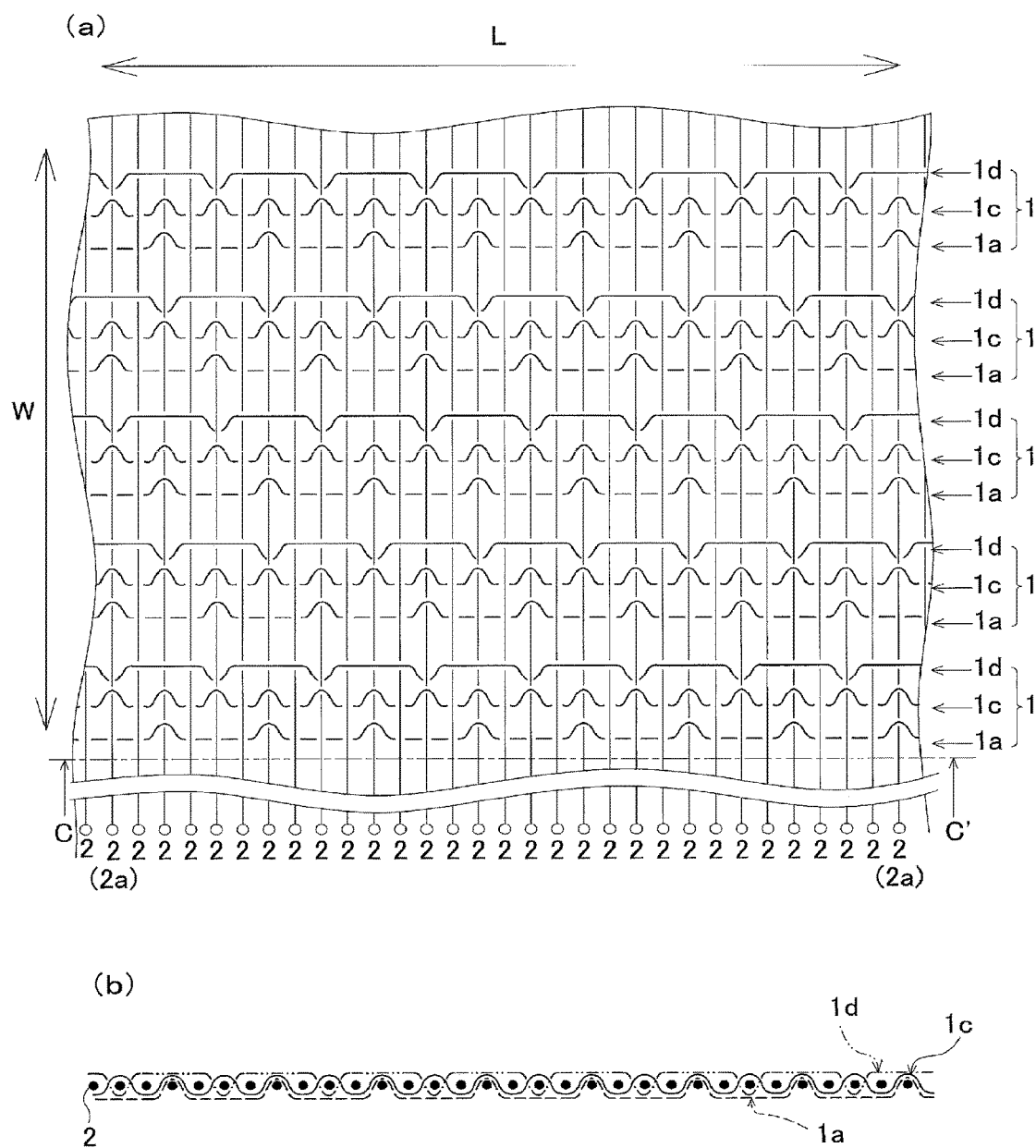
FIG. 8(a) is an explanatory diagram for describing an example of a fabric weave of a front ground face of a main body part which does not have a loop face of a touch fastener.
FIG. 8(b) is a cross-sectional view taken along line C-C' and viewed in the direction of an arrow, of the fabric weave shown in FIG. 8(a).

That is, the warp 1 is provided with the first warp ground yarn 1*a* which configures one face (for example, the back ground face) of the fabric along with the weft 2, the elastic yarn 1*c* which provides stretchability in the warp direction, and the second warp ground yarn 1*d* which configures the other face (for example, the front ground face) of the fabric along with the weft 2, as shown in FIG. 8.

Further, the weft 2 is provided with the weft ground yarn 2*a* which configures the back ground face of the fabric along with the first warp ground yarn 1*a*.

Further, in FIGS. 8(*b*) and 9(*b*), on the basis of the wefts 2 which are provided in parallel, the upper side is the front ground face and the lower side is the back ground face.

Further, in the main body part 10, the pattern 14 composed of characters, figures, symbols, or a combination thereof can be partially formed in the front ground face in a jacquard weave which is freely opened, by making the first warp ground yarn 1*a* (for example, a green yarn) of the warp 1 float to the front ground face side (and making the second warp ground yarn 1*d* (for example, a black yarn) sink to the back ground face side) with respect to a plurality of wefts 2 adjacent to each other in the warp direction (the longitudinal direction L) by using a jacquard needle loom.

Next, an example of a fabric weave according to this embodiment will be described by using FIG. 8. That is, the first warp ground yarn 1*a* configures a fabric weave by repeating 1-3 float-sink with respect to the weft 2 (the weft ground yarn 2*a*), in which the first warp ground yarn 1*a* floats so as to pass on the upper side with respect to a single piece of weft 2 (weft ground yarn 2*a*) and sinks so as to pass on the lower side with respect to three pieces of wefts 2 (weft ground yarns 2*a*) adjacent to each other, as shown in FIG. 8(*b*).

Further, the elastic yarn 1*c* configures a fabric weave by repeating 1-1 float-sink with respect to the weft 2 (the weft ground yarn 2*a*), in which the elastic yarn 1*c* floats so as to pass on the upper side with respect to a single piece of weft 2 (weft ground yarn 2*a*) and sinks so as to pass on the lower side with respect to a single piece of weft 2 (weft ground yarn 2*a*), as shown in FIG. 8(*b*).

Further, the second warp ground yarn 1*d* configures a fabric weave by repeating 3-1 float-sink with respect to the weft 2 (the weft ground yarn 2*a*), in which the second warp ground yarn 1*d* floats so as to pass on the upper side with respect to three pieces of wefts 2 (weft ground yarns 2*a*) adjacent to each other and sinks so as to pass on the lower side with respect to a single piece of weft 2 (weft ground yarn 2*a*), as shown in FIG. 8(*b*).

In addition, the fabric weave composed of the first warp ground yarn 1*a*, the elastic yarn 1*c*, and the second warp ground yarn 1*d* shown in FIG. 8 is an example, and there is no limitation to this fabric weave.

Subsequently, an example of a fabric weave of a pattern part according to this embodiment will be described by using FIG. 9. That is, the first warp ground yarn 1*a* forming the pattern 14 configures a fabric weave by repeating 3-1 float-sink with respect to the weft 2 (the weft ground yarn 2*a*), in which the first warp ground yarn 1*a* floats so as to pass on the upper side with respect to three pieces of wefts 2 (weft ground yarns 2*a*) adjacent to each other and sinks so as to pass on the lower side with respect to a single piece of weft 2 (weft ground yarn 2*a*), as shown in FIG. 9(*b*).

Further, the elastic yarn 1*c* forming the pattern 14 configures a fabric weave by repeating 1-1 float-sink with respect to the weft 2 (the weft ground yarn 2*a*), in which the elastic yarn 1c floats so as to pass on the upper side with respect to a single piece of weft 2 (weft ground yarn 2a) and sinks so as to pass on the lower side with respect to a single piece of weft 2 (weft ground yarn 2a), as shown in FIG. 9(b).

Further, the second warp ground yarn 1d forming the pattern 14 configures a fabric weave by repeating 1-3 float-sink with respect to the weft 2 (the weft ground yarn 2a), in which the second warp ground yarn 1d floats so as to pass on the upper side with respect to a single piece of weft 2 (weft ground yarn 2a) and sinks so as to pass on the lower side with respect to three pieces of wefts 2 (weft ground yarns 2a) adjacent to each other, as shown in FIG. 9(b).

Figure 9:
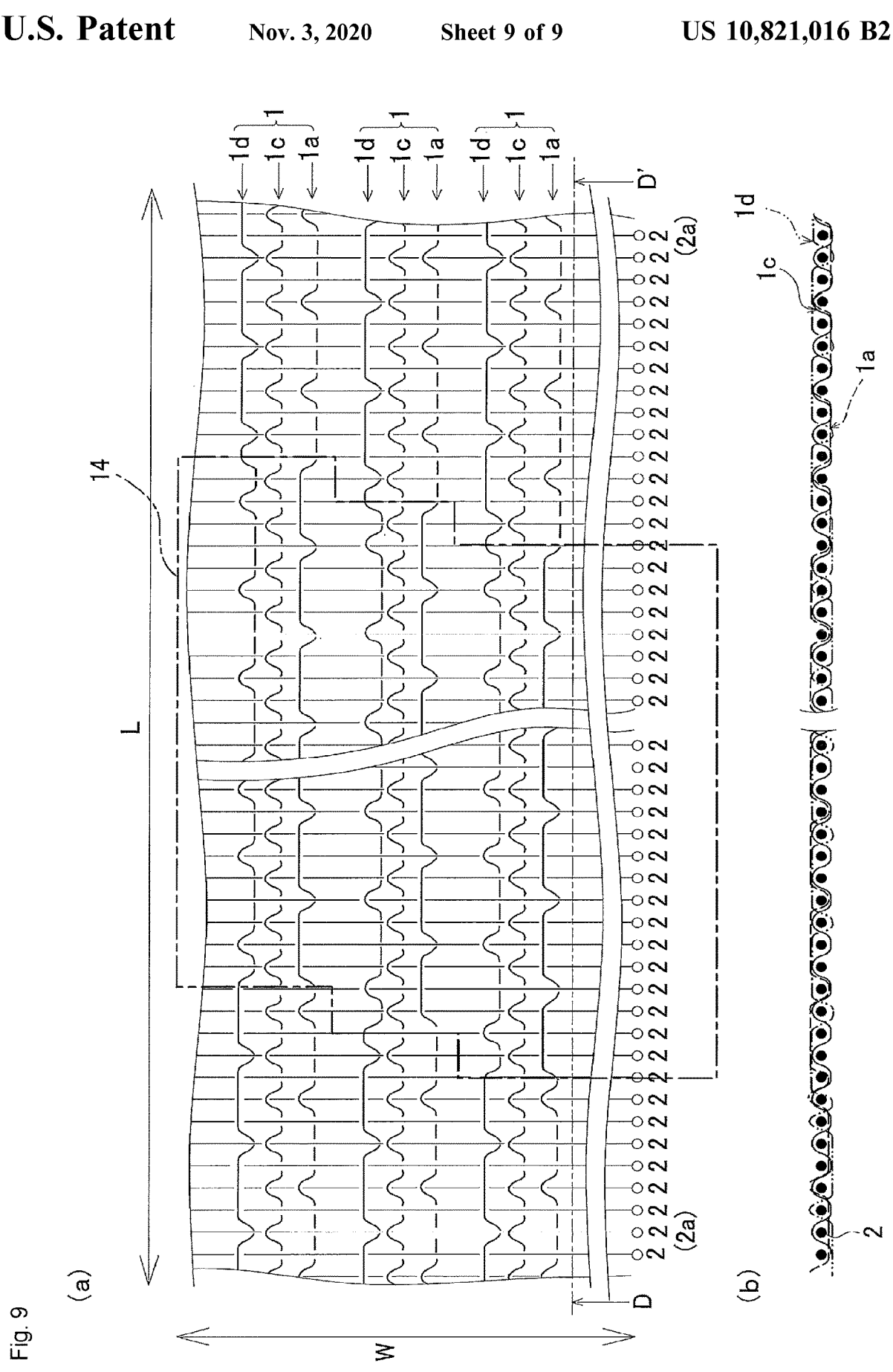
FIG. 9(a) is an explanatory diagram for describing an example of a fabric weave of a pattern part of the main body part which does not have a loop face of a touch fastener.
FIG. 9(b) is a cross-sectional view taken along line D-D' and viewed in the direction of an arrow, of the fabric weave shown in FIG. 9(a).

In addition, the fabric weave composed of the first warp ground yarn 1a, the elastic yarn 1c, and the second warp ground yarn 1d shown in FIG. 9 is an example, and as long as it is possible to form the pattern 14 in the front ground face, there is no limitation to this fabric weave.

Here, an embodiment in which the main body part 10 is a stretchable fabric which does not have the loop face 13 of a touch fastener and the maximum elongation is set to be 60% (1.60 times±0.1) will be described.

With respect to each of the first warp ground yarn 1a and the second warp ground yarn 1d of the main body part 10 according to this embodiment, a woolly nylon two-ply yarn having a thickness of 100 deniers is preferable, and in the main body part 10 according to this embodiment, it is preferable to use 152 pieces of woolly nylon two-ply yarns for each of the first warp ground yarn 1a and the second warp ground yarn 1d.

Further, with respect to the elastic yarn 1c of the main body part 10 according to this embodiment, a covering yarn obtained by covering a polyurethane yarn (for example, a polyurethane elastic fiber "Lycra (registered trademark) fiber" of Toray Opelontex Co., Ltd.) having a thickness of 560 deniers with two pieces of polyester woolly (EW) single yarns each having a thickness of 150 deniers is preferable, and in the main body part 10 according to this embodiment, it is preferable to use 41 pieces of covering yarns.

Further, with respect to the weft ground yarn 2a of the main body part 10 according to this embodiment, it is preferable to use a single piece of polyester woolly yarn (EW) having a thickness of 150 deniers.

Further, in the main body part 10 according to this embodiment, a single piece of weft ground yarn 2a is picked as the weft 2 by a power loom, and the number of times of picking (the number) of the weft 2 (the weft ground yarn 2a) is 33.6 times (33.6 pieces) per 2.54 cm (1 inch).

In this manner, in the main body part 10 according to this embodiment, due to the quality of the materials of the warp 1 and the weft 2 (in particular, the thicknesses of the elastic yarn 1c and the weft ground yarn 2a) described above and the number of times of picking (the number) of the weft 2 described above, it is possible to set the maximum elongation in the warp direction (the longitudinal direction L) to be 60%.

Further, the main body part 10 according to this embodiment has a mixing ratio of nylon: 47%, polyester: 44%, and polyurethane: 9%. However, there is no limitation to this mixing ratio.

Here, in the wrist joint bandage 100 according to this embodiment, it is necessary to wind the main body part 10 around the wrist of a wearer and then making the engaging part 30 (the hook face 33 of a touch fastener) which is located at the other end 10b of the main body part 10 be engaged with the main body part 10.

For this reason, in a case where the main body part 10 which does not have the loop face 13 of a touch fastener is used in the wrist joint bandage 100, a separate member having the loop face of a touch fastener is provided in a corresponding range of the front ground face of the main body part 10 (the winding part 11), with which the engaging part 30 is engaged.

In particular, in a case where a separate member is provided at the main body part 10, the expansion and contraction of the main body part 10 is inhibited by the separate member. However, in a portion of the area of the winding part 11 which has circled around the wrist of a wearer on the basis of the thumb, the expansion and contraction of the winding part 11 is not very required, and therefore, it is preferable to provide the separate member at the area of the winding part 11.

Further, a case where the wrist joint bandage 100 according to this embodiment is directly wound on the bare skin has been described. However, with respect to the wrist joint on which, for example, a hand joint supporter disclosed in Pamphlet of International Publication No. WO/2011/090192 or a glove is worn, the wrist joint bandage 100 is wound on the hand joint supporter or the glove, thereby eliminating the slip of the wrist joint bandage 100 with respect to the bare skin, whereby it is possible to improve the operation and effects of the wrist joint bandage 100.

Further, in a case where the wrist joint bandage 100 is wound on the glove, it is also possible to provide the wrist joint bandage 100 and the glove as a set.

Further, in a case where the wrist joint bandage 100 is wound on the glove (a glove in which the maximum elongation is low is preferable), as an aspect of the wrist joint bandage 100, the anchor part 20 of the wrist joint bandage 100 is removed from the main body part 10 and one end 10a of the main body part 10 is sewn to the vicinity of the base of the thumb of the glove, whereby it is possible to make the thumb of the glove function as the anchor part 20.

REFERENCE SIGNS LIST

1: warp
1a: warp ground yarn (first warp ground yarn)
1b: pile yarn
1c: elastic yarn
1d: second warp ground yarn
2: weft
2a: weft ground yarn
2b: fusion yarn
10: main body part
10a: one end
10b: other end
11: winding part
12: supporting part
13: loop face
14: pattern
20: anchor part
21: one end
22: other end
30: engaging part
31: rectangular portion
32: isosceles trapezoid portion
33: hook face
40: joining portion
100: wrist joint bandage

The invention claimed is:

1. A wrist joint bandage, comprising:
a main body part comprising a woven fabric and having a band shape and a loop face;
an anchor part joined to one end of the main body part and having a band-shaped body forming a ring shape such that the anchor part is configured to insert a finger of a wearer; and
an engaging part joined to the other end of the main body part and having a hook face such that the hook face detachably sticks to the loop face of the main body part,
wherein the main body part has a winding part on one end side of the main body part and a supporting part on the other end side such that the winding part has a straight line shape and is configured to wind around a wrist of the wearer and that the supporting part has a straight line shape and is configured to extend from the back of the hand or the palm to the wrist of the wearer, the supporting part and the winding part have the straight line shapes having the same width, the band-shaped body of the anchor part has two opposite ends joined to the one end of the main body part such that one of the two opposite ends is directly joined to a first portion of the one end of the main body part and the other one of the two opposite ends is directly joined to a second portion of the one end of the main body part, and the anchor part has a maximum elongation in a circumferential direction of the anchor part that is greater than a maximum elongation in a longitudinal direction of the main body part.

2. The wrist joint bandage according to claim 1, wherein the main body part has a maximum elongation in a range of 40% to 80% in a longitudinal direction of the main body part.

3. The wrist joint bandage according to claim 2, wherein the anchor part has the two opposite ends forming a joining portion joined to the first and second portions of the one end of the main body part and sewn in a convex shape toward an anchor part side such that the convex shape is longer than a length in a width direction of the main body part.

4. The wrist joint bandage according to claim 3, wherein the main body part, anchor part and engaging part are configured to be worn on the wrist of the right hand or left hand of the wearer.

5. The wrist joint bandage according to claim 2, wherein the main body part, anchor part and engaging part are configured to be worn on the wrist of the right hand or left hand of the wearer.

6. The wrist joint bandage according to claim 2, wherein the main body part has a front ground face having a pattern including at least one of character, a figure and a symbol.

7. The wrist joint bandage according to claim 2, wherein the main body part has a front ground face side and a back ground face side such that the loop face is formed on the front ground face side, and the anchor part has a substantially conical tube form having a tapered shape such that the anchor part has a small-diameter portion formed on the front ground face side of the main body part and a large-diameter portion formed on the back ground face side of the main body part.

8. The wrist joint bandage according to claim 1, wherein the anchor part has the two opposite ends forming a joining portion joined to the first and second portions of the one end of the main body part and sewn in a convex shape toward an anchor part side such that the convex shape is longer than a length in a width direction of the main body part.

9. The wrist joint bandage according to claim 8, wherein the main body part, anchor part and engaging part are configured to be worn on the wrist of the right hand or left hand of the wearer.

10. The wrist joint bandage according to claim 8, wherein the main body part has a front ground face having a pattern including at least one of character, a figure and a symbol.

11. The wrist joint bandage according to claim 8, wherein the main body part has a front ground face side and a back ground face side such that the loop face is formed on the front ground face side, and the anchor part has a substantially conical tube form having a tapered shape such that the anchor part has a small-diameter portion formed on the front ground face side of the main body part and a large-diameter portion formed on the back ground face side of the main body part.

12. The wrist joint bandage according to claim 1, wherein the main body part, anchor part and engaging part are configured to be worn on the wrist of the right hand or left hand of the wearer.

13. The wrist joint bandage according to claim 12, wherein the main body part has a front ground face having a pattern including at least one of character, a figure and a symbol.

14. The wrist joint bandage according to claim 12, wherein the main body part has a front ground face side and a back ground face side such that the loop face is formed on the front ground face side, and the anchor part has a substantially conical tube foil having a tapered shape such that the anchor part has a small-diameter portion foil ied on the front ground face side of the main body part and a large-diameter portion formed on the back ground face side of the main body part.

15. The wrist joint bandage according to claim 1, wherein the main body part has a front ground face having a pattern including at least one of character, a figure and a symbol.

16. The wrist joint bandage according to claim 1, wherein the main body part has a front ground face side and a back ground face side such that the loop face is formed on the front ground face side, and the anchor part has a substantially conical tube form having a tapered shape such that the anchor part has a small-diameter portion formed on the front ground face side of the main body part and a large-diameter portion formed on the back ground face side of the main body part.

17. The wrist joint bandage according to claim 1, wherein the engaging part is joined to the other end of the main body part and has a protruding portion such that the protruding portion is protruding from the other end of the main body part.

18. The wrist joint bandage according to claim 17, wherein the engaging portion has a rectangular portion sewn to a back ground face of the main body part and an isosceles trapezoid portion forming the protruding portion protruding from the other end of the main body part.

19. The wrist joint bandage according to claim 17, wherein the main body part has a maximum elongation in a range of 40% to 80% in a longitudinal direction of the main body part.

20. The wrist joint bandage according to claim 17, wherein the anchor part has the two opposite ends forming a joining portion joined to the first and second portions of the one end of the main body part and sewn in a convex shape toward an anchor part side such that the convex shape is longer than a length in a width direction of the main body part.

* * * * *